(12) United States Patent
Arter et al.

(10) Patent No.: US 7,378,057 B2
(45) Date of Patent: May 27, 2008

(54) EVAPORATION CONTROL FOR A FLUID SUPPLY

(75) Inventors: Thomas Arter, Rochester, NY (US);
Scott Schwallie, Rochester, NY (US);
James Hassett, Williamson, NY (US);
James Love, Penfield, NY (US); James D. Shaw, Rochester, NY (US); Donald J. Moran, Jr., Rochester, NY (US);
Robert T. Witkowski, Leroy, NY (US);
Malinda L. McFeaters, Rochester, NY (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 204 days.

(21) Appl. No.: 10/394,825

(22) Filed: Mar. 21, 2003

(65) Prior Publication Data
US 2003/0223914 A1 Dec. 4, 2003

Related U.S. Application Data

(60) Provisional application No. 60/369,220, filed on Apr. 1, 2002.

(51) Int. Cl.
*B01L 3/02* (2006.01)
(52) U.S. Cl. ............... 422/100; 422/63; 422/64; 422/65; 422/99; 422/101; 436/180; 222/416; D7/300
(58) Field of Classification Search .......... 422/99–101, 422/63–65; D9/306; 436/180; 99/275; 220/62.11; 215/386; 222/416; D7/300
See application file for complete search history.

(56) References Cited

U.S. PATENT DOCUMENTS

| 512,874 | A | * | 1/1894 | Fraser .................. 422/102 |
| 3,680,330 | A | * | 8/1972 | Canosa ................ 62/457.3 |
| 3,853,217 | A | | 12/1974 | Scordato et al. |
| 4,055,273 | A | * | 10/1977 | Jones .................. 220/631 |
| 4,130,978 | A | | 12/1978 | Cohen |
| 4,220,258 | A | * | 9/1980 | Gruenewald ........... 222/46 |
| 5,102,631 | A | | 4/1992 | Jordan et al. |
| 5,635,137 | A | | 6/1997 | Manz et al. |
| D380,553 | S | | 7/1997 | Riekkinen |
| 5,874,048 | A | | 2/1999 | Seto et al. |
| 6,375,028 | B1 | * | 4/2002 | Smith ................. 220/258.1 |

FOREIGN PATENT DOCUMENTS

DE 195 36 789 4/1997
FR 1404672 5/1965

OTHER PUBLICATIONS

Aldrich Chemical Company, 1988, p. 2191.*

* cited by examiner

*Primary Examiner*—Jill Warden
*Assistant Examiner*—Jyoti Nagpaul

(57) ABSTRACT

Evaporation control for a fluid supply, such as used in a clinical analyzer, can be provided by utilizing a straw-like insert which is disposed into a fluid-containing bottle. The straw provides an increased diffusion length or "stagnant" zone. The bottle can also be configured to effectively reduce evaporation in a similar manner by providing a narrowed diameter prior to the fluid retaining portion of the bottle and by increasing the distance between the top of the bottle and the top of the fluid surface.

5 Claims, 8 Drawing Sheets

EVAPORATION CONTROL FOR A FLUID SUPPLY

This application claims priority, under 35 U.S.C.§119(e), of U.S. Provisional Application Ser No. 60/369,220, filed Apr. 1, 2002, entitled: "Evaporator Control For A Fluid Supply".

FIELD OF THE INVENTION

This invention relates generally to the field of clinical chemistry, and more particularly to a fluid supply for a clinical analyzer or similar apparatus having improved features for controlling evaporation.

BACKGROUND OF THE INVENTION

Clinical chemistry analyzers, such as those manufactured by Abbott Laboratories and the Johnson and Johnson Company, among others, having reagent supplies on board for use in preparing wet immunoassays are sensitive to the effect of reagent evaporation, thereby causing prediction shifts with storage time. The change in the concentration of reagents that occurs with evaporation causes the reaction concentrations in a reaction vessel, such as a cuvette, to change, thereby causing the prediction shifts. Assay systems with a large reagent concentration sensitivity, such as EMIT TDM assays, for example, need effective evaporation control to achieve acceptable onboard stability times. Stability goals require that reagents be stable for 2 or more weeks onboard a clinical analyzer.

Most known "wet" analyzer systems use one of three methods to control such evaporation effects, as found with reagent supplies containing a plurality of bottles of at least one reagent. The first method is to package large volume reagent bottles on board and to use relatively large amounts of fluid in each test. This method does not reduce evaporation, but the effect is spread across a large fluid volume so that the effect on reagent concentration is minimized. This method of control requires a large reagent storage area within the analyzer and increases the cost per test as more fluid is used in each test.

A second method of evaporation control is to cap the reagent bottles between each use. This method does reduce evaporation effects, but only while the bottles are capped, and further requires a cap opening mechanism which must be disposed within the analyzer to open and close the caps between uses. This mechanism and its associated control adds significantly to the overall cost and complexity of the analyzer. In addition, evaporation still occurs as each bottle opening operation tends to flush out air contained in the bottle and in fact, actually increases or promotes evaporation. A more expensive bottle design is also needed using this method, as the bottle caps that are used during long-term storage must be compatible with the bottle opening mechanism.

A third known evaporation control method is to restrict the size of the metering access hole in the top of the reagent supply bottle. The bottles are stored uncapped within the reagent supply and using a small diameter hole reduces evaporation out of the reagent supply. This form of control works well with syringe metering systems that utilize relatively narrow metal tubes (~2 mm in diameter), but a metering system using disposable metering tips having larger diameters on the order of about 10 mm or more requires a reagent bottle(s) having a relatively large accommodating metering access hole or opening which does not control evaporation acceptably. In addition, the diameter of the necks of the larger diameter reagent bottles must also be large enough to accept a relatively large metering tip and associated mechanism which passes into the bottle interior in order to aspirate fluid therefrom.

SUMMARY OF THE INVENTION

It is therefore a primary object of the invention to overcome the above-noted deficiencies of the prior art.

It is another primary object of the present invention to improve or minimize evaporation, and hence evaporation-related effects, from reagent or other fluid supplies used in conjunction with a clinical analyzer.

The invention features a design which is useful for reagent or other fluid containing bottles for use in a clinical analyzer, the bottles requiring relatively large diameter holes, as required, for example, to permit aspiration using a large diameter (those having a maximum diameter of about 8 mm) metering element.

According to one preferred aspect, an evaporation control element is placed into the bottle interior. This control element is preferably a narrow tube that reduces the wetted surface area exposed to the environment (e.g., the reagent supply) such that only the surface area at the bottom of the tube is exposed to the outside environment. That is, contained fluid on the outside of the inserted tube is effectively capped from evaporative effects. The narrow tube, when inserted, creates a diffusion zone or area that effectively increases the distance of the fluid surface away from the top of the bottle. It has now been determined that this increase in distance is a very significant factor in controlling evaporation, and can in fact be a potentially stronger control than simply decreasing the amount of exposed or wetted fluid surface area in the fluid supply. As a result, a bottle design can be contemplated that contains a relatively broad well of fluid at the bottom of a long tube. The evaporation control element is used in conjunction with a sealed or pierceable bottle in which the element is effectively mated thereto, or the element is sized at the bottle opening to cover the entire open end of a bottle.

It has further been determined that decreasing the diameter of the long tube also decreases the evaporation present. According to a preferred embodiment, and in order to achieve the mutual goals of minimum surface area exposed, an extended distance between the fluid surface and the top of the bottle, and a minimum tube diameter, a narrow tube was designed to fit into a large diameter bottle opening such that: i). most of the fluid was at the bottom of the bottle, ii). the tube penetrated into the fluid surface to further reduce exposed wetted surface area, and iii). the diameter of the tube at its bottom was further restricted, but sufficient to permit metering.

The tube preferably includes at least one vent hole to permit trapped air within the bottle to be vented when the tube is initially inserted. The tube is preferably inwardly tapered to a minimum diameter or preferably can include a substantially parallel wall construction having a minimum diameter. To ease automation in inserting a tube into the interior of a bottle, the tube can include a stepped section adjacent the bottom of the tube. This feature provides a contacting surface for an inserting device to push against and also reduces the surface area of fluid which is exposed to the environment at low fill volumes.

The tube can also include at least one outer rib to permit a supply of tubes to be stored and easily removed from one another in a stacked arrangement. The ribs prevent jamming and further provide a means for controlling the insertion depth while stacked.

According to another preferred aspect of the invention, a bottle can be designed in lieu of providing a narrow tubular evaporation control element. The bottle can include an inwardly tapering upper and intermediate portion that terminates in a relatively wide bottom fluid retaining portion. The diameter is sufficiently narrowed to permit the passage of a metering element, such as a disposable metering tip, in which a stagnant diffusion zone is produced, preferably immediately above the contained fluid, to significantly reduce evaporative effects without requiring a capping mechanism.

Alternatively, the bottle can assume a somewhat parallel wall construction in the upper and intermediate portions having a minimum diameter to permit metering, increasing the length of the stagnant diffusion zone.

An advantage of the present invention, using an evaporation straw or similar evaporation control means, is substantially lower cost and complexity to a clinical analyzer design, while permitting large diameter supply bottles to be utilized without capping of same for each use. In addition, a fluid supply having evaporation control features in accordance with the present invention is in fact superior than most known bottle designs having pierceable caps.

Employing the present invention as described herein minimizes the exposed wet surface area of a contained fluid and also maximizes the path length between the fluid surface and the top opening of the bottle such that effective evaporation control can be maintained, even with large diameter bottle openings.

These and other objects, features, and advantages will become apparent from the following Detailed Description which should be read in conjunction with the accompanying drawings.

DETAILED DESCRIPTION

Figure 1:
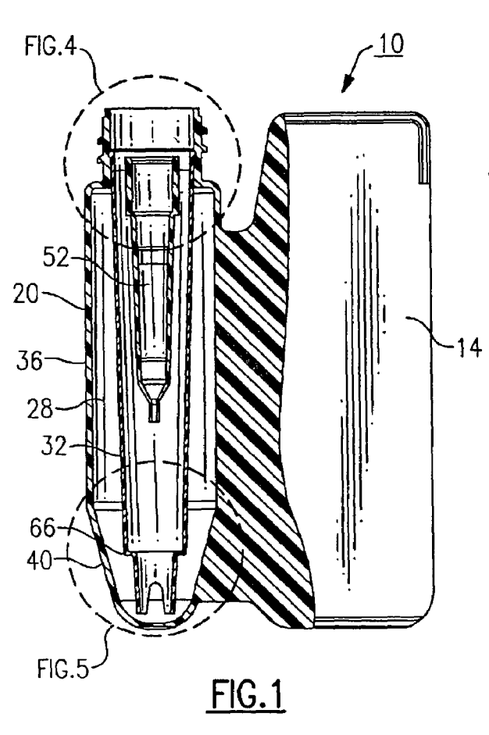
FIG. 1 is a side elevational view, shown in section, of a fluid supply made in accordance with a preferred embodiment of the present invention.

FIG. 1 depicts a reagent pack 10 that is sized to be fitted into a rotatable wheel of a reagent supply of a clinical analyzer. The reagent pack 10 is made from an moldable bio-compatible plastic material and comprises a support 14 that includes an integral bottle 20. The bottle 20 includes a top opening 24, shown in FIG. 4, extending into a hollow interior 28 for retaining a volume of fluid, such as a reagent used in preparing immunoassays. An evaporation control element 32 is sized to be fitted into the bottle interior 28. According to this particular embodiment the bottle 20 has a total height of approximately 85 mm and an inside diameter of approximately 19.5 mm. It should be noted that the above specifications are intended to be exemplary and not in any way to be limiting of the invention.

Figure 4:
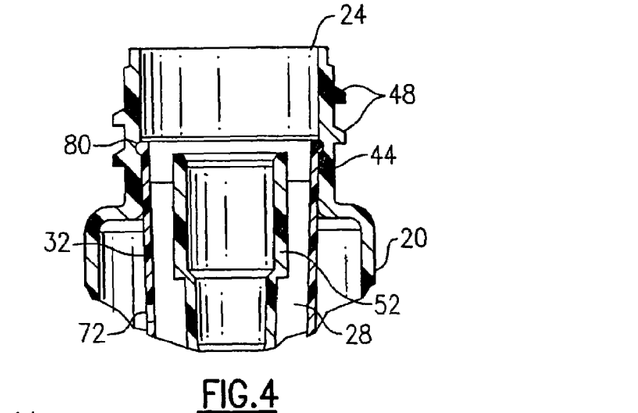
FIG. 4 is an enlarged view of the top of the fluid supply of FIG. 1.
Figure 5:
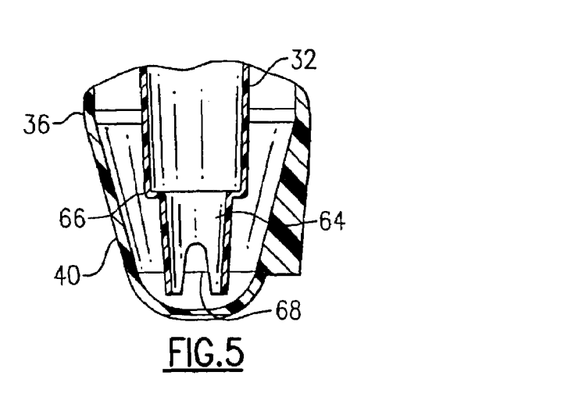
FIG. 5 is an enlarged view of the bottom of the fluid supply of FIG. 1.
Figure 14:
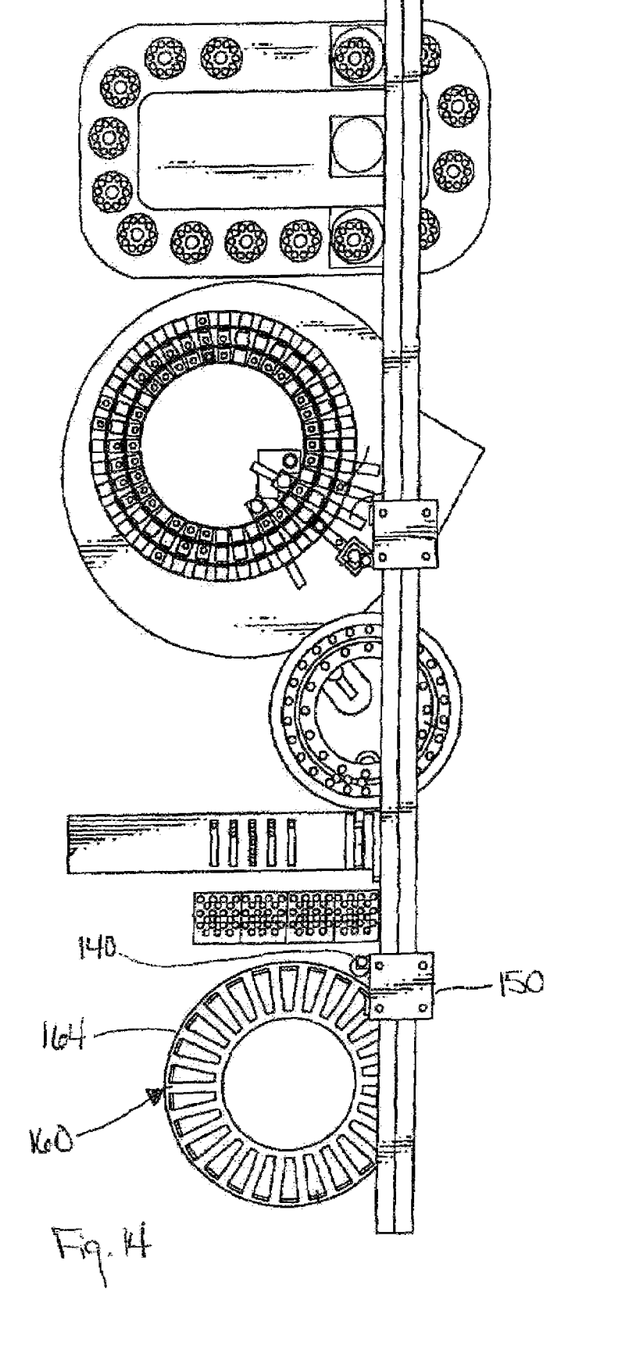
FIG. 14 is a top perspective view of a clinical analyzer including a reagent supply.
Figure 15:
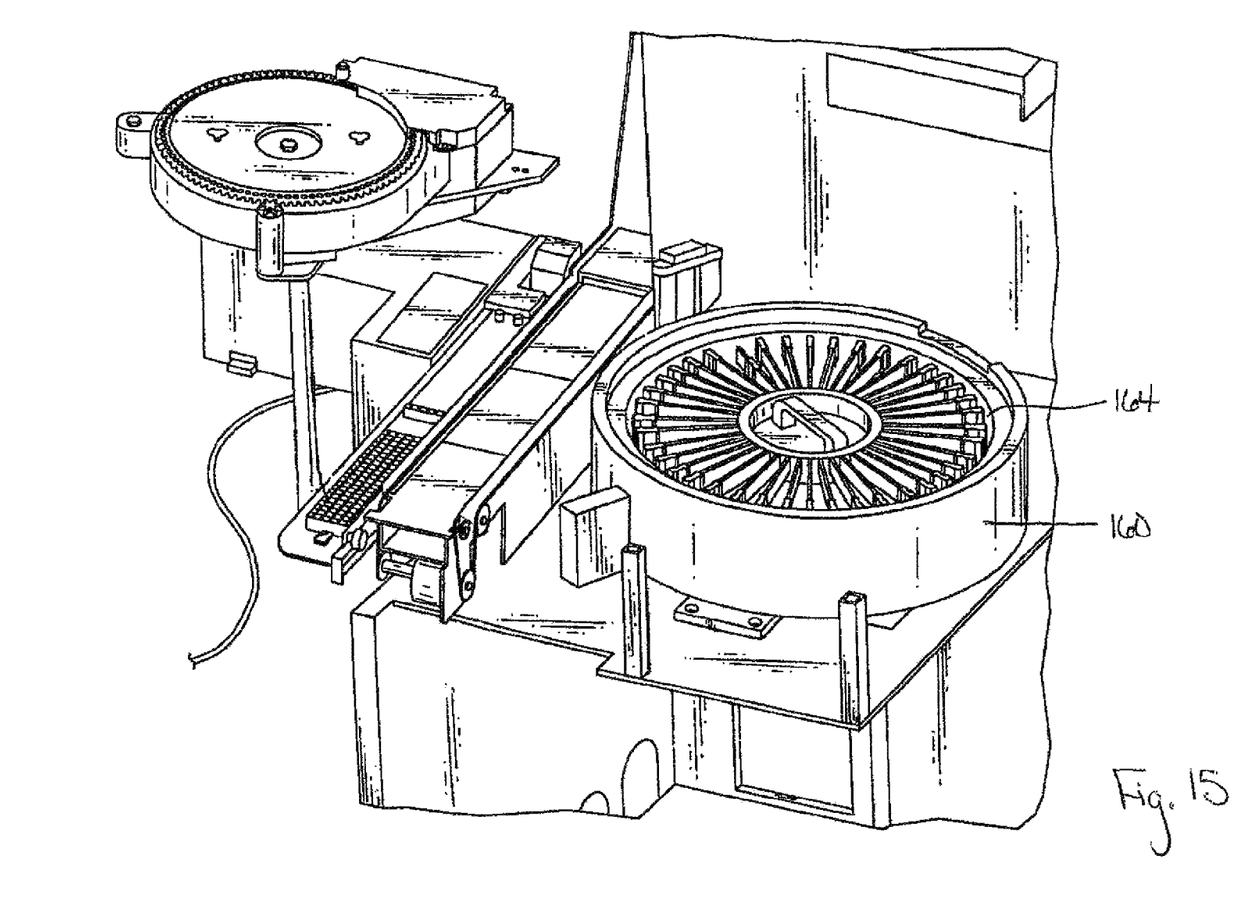
FIG. 15 is a side view of a metering mechanism for retaining a fluid aspirating/dispensing element that can be placed into the fluid supply.

The bottle 20 includes a cylindrical wall 36 that extends from a tapered bottom 40 to a top necked portion 44, FIG. 4, having exterior cap threads 48, FIG. 4. Referring to FIGS. 14 and 15, the reagent supply 160 includes a cover (not shown in these views for clarity) that includes a metering opening (not shown) which permits the passage of a fluid aspirating/dispensing member, such as a disposable metering tip 52, FIG. 1. For purposes of this description, a "metering tip" refers to a fluid aspirating/dispensing member that can be attached to a proboscis 140, typically shown in FIG. 16, as used in a metering mechanism 150 as described for example, in commonly owned U.S. patent application No. 10/185,613, filed Jun. 28, 2002, the entire contents of which are herein incorporated by reference. As shown in FIG. 1, the disposable metering tip 52 includes an open upper end and a lower dispense end and is capable of retaining a volumetric or micro-volumetric quantity of fluid. Metering tips in and of themselves are repletely well known in the field and do not form a specific part of the present invention. For the sake of this embodiment, the metering tip 52 described herein is a disposable plastic member manufactured by Ortho Clinical Diagnostics, Inc. under the trade name of Vitros$^{TM}$, though it will be apparent that other suitable fluid dispensing/aspirating members can be substituted.

Temperature and humidity control systems (not shown) are also provided within the reagent supply 160, FIGS. 14, 15, for maintaining a relatively constant environment for a plurality of supported reagent packs 10. In use, the clinical analyzer rotates the wheel 164 of the reagent supply 160 until the top opening 24 is aligned with the metering opening (not shown) and a metering mechanism 150, FIG. 16, raises and lowers the disposable metering tip 52 into the confines of the bottle interior 28. A predetermined volume of fluid is then aspirated into the metering tip 52 and the tip is withdrawn by the metering mechanism.

Figure 16:
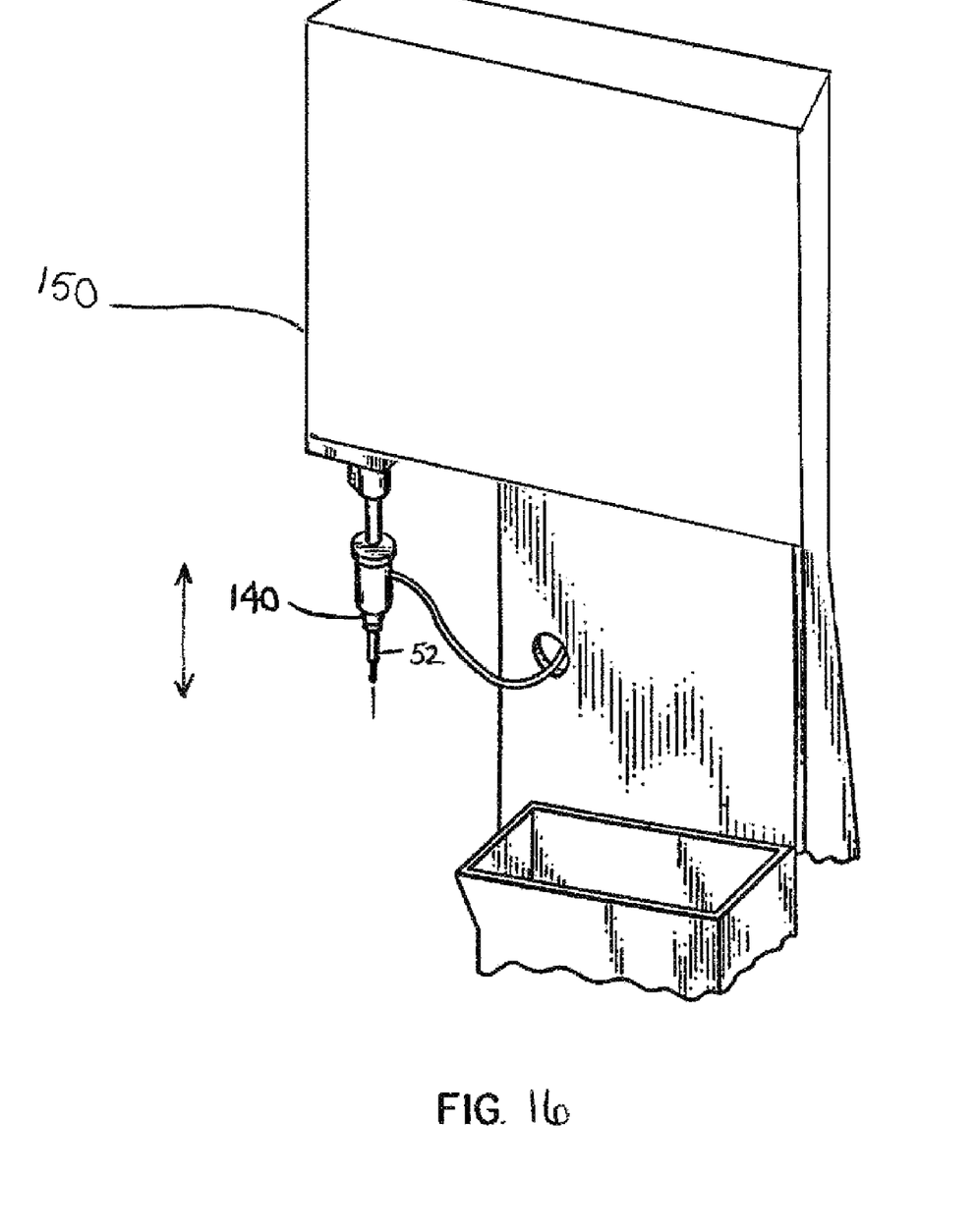
FIG. 16 is a top perspective view of a metering apparatus including a proboscis having a metering tip attached.

The functions and structure of the reagent wheel 164 and reagent supply 160 and the metering mechanism 150, FIG.

16, for a wet chemistry clinical analyzer are commonly known and are not considered part of the invention. Therefore, discussion of same is not required except as required in order to understand the invention. It should also be pointed out that though a single bottle reagent pack is exemplarily illustrated in FIG. 1, it should be readily apparent that can these packs can include two or more bottles, either integrally molded with the support or releasably attachable thereto.

As shown in FIGS. 1-4, the evaporation control element, hereinafter synonymously referred to as an evaporation straw, is inserted into the bottle interior 28. The evaporation straw 32 which includes a pair of open ends and is essentially hollow, is preferably made from a plastic molded material and includes an upper end 33 which when inserted into the bottle 20 creates an interference fit with the inside of the top necked portion 44 and is suspended into the bottle. According to this embodiment, the upper end 33 of the evaporation straw 32 includes an annular tab 76 that engages a circumferential slot 80 provided in the top necked portion 44 of the bottle 20. The inside diameter of the evaporation straw 32 has a narrowed tubular construction which tapers down, according to this specific embodiment, from a diameter of approximately 13 mm at the upper end 33 of the straw to a diameter of approximately 5 mm at an opposing bottom end 35. The overall length of the evaporation straw 32 used according to this embodiment is approximately 72 mm and therefore the bottom of the straw reaches to within approximately 1.5 mm of the bottom of the bottle interior 28. The evaporation straw 32 can also touch the bottom of the bottle if need be, as aligned cutouts 68 allow fluid movement around the end of the evaporation straw 32.

Figure 2:
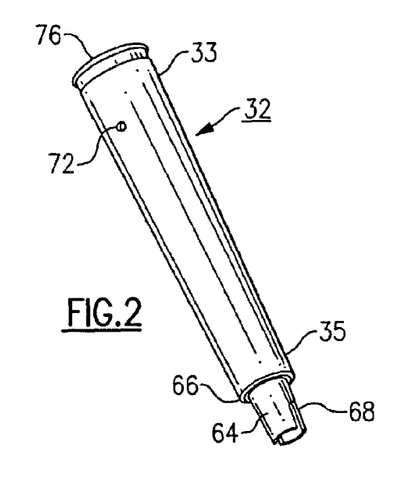
FIG. 2 is a side elevational view of an evaporation control element that is inserted into the fluid supply of FIG. 1.
Figure 3:
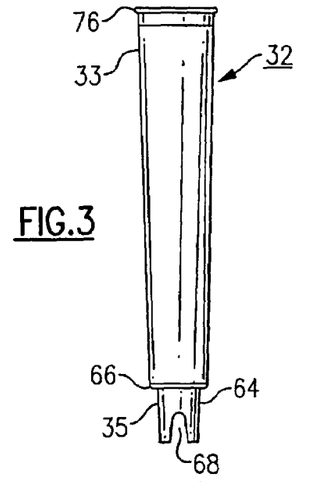
FIG. 3 is a rotated perspective view of the evaporation control element depicted in FIGS. 1 and 2.

Referring to FIGS. 1-3, the bottom end 35 of the evaporation straw 32 includes a narrowed bottom section 64 including a stepped portion 66 that permits the straw to be inserted into the bottle 20 initially. In order to release air which might otherwise remain trapped within the bottle 20 when the evaporation straw 32 is first inserted, the narrowed bottom section 64 of the evaporation straw includes a pair of aligned cutouts 68 which provide a path for air to circulate out of the bottle interior 28 when the evaporation straw 32 is first inserted, the straw further including at least one intermediate vent hole 72 adjacent the top thereof. The vent hole 72 permits quicker filling of the bottles after the straw has been inserted, the vent hole allowing the fluid levels to equilibrate between the inner and outer areas of the straw without significantly adding to evaporative effects. Preferably and according to this example, a suitable vent hole area is less than 4 square millimeters.

Fluid fill levels of greater than 100 μL will touch the bottom of the evaporation straw 32 so that a large fraction of the fluid's top surface is not exposed to the top opening 28 (e.g., the fluid is outside of the straw and inside the outer walls of the bottle and is thus effectively "capped"). The bottom of the bottle 20 can be tapered as shown to minimize the amount of fluid waste that would occur in use by maximizing the fluid height in the bottle at low total volumes to allow metering to occur.

In passing, it should be noted that the straw can assume alternate constructions. According to another preferred design, the straw can have a narrow tubular construction having as narrow a diameter as needed to permit a metering element to pass therethrough or at a minimum for the distal tip thereof to reach the fluid surface for aspiration. A typical metering element, as described herein has a maximum diameter of about 8 mm. Preferably, some widening of the diameter is provided at the top thereof to account for steering and locating of the metering element by the metering mechanism of the analyzer.

EXAMPLE A

Figure 6:
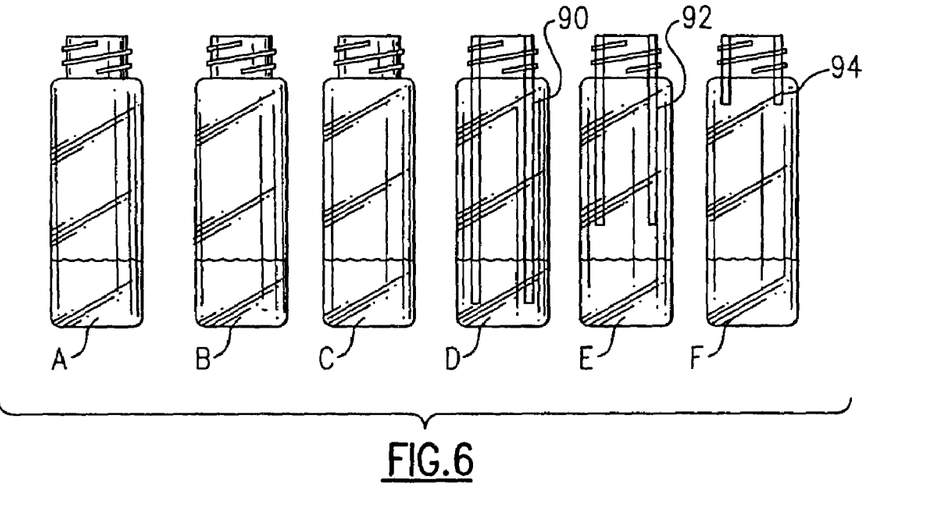
FIG. 6 is a front view of a first plurality of fluid supply designs having varying evaporative control features.

Comparison of Evaporation Effects Based on Differing Straw Lengths and Prior Known Evaporation Controls As a prologue to the fluid supply illustrated in FIGS. 1-5, and to further point out the inventive concepts achieved by the evaporation control member, a first plurality of different 20 mL bottles, see FIG. 6, were each filled, according to this example, with 4 mL each of a solution of 0.004% Magenta dye in water. This solution produces a measurable absorbance of roughly 2 AU at a wavelength of 540 nanometers. By tracking changes in the absorbance of the solution over time using a spectrophotometer or similar apparatus, changes in the absorbance of the solution and effectively, evaporation rates can be extrapolated which provides a basis for tangible comparison.

In this example, six (6) bottle designs were tested and compared. These bottles are shown in FIG. 6 and included the following: a standard open bottle, herein designated A, a bottle having a plastic pierceable cap with flexible flaps, herein designated B, a bottle having a foil pierceable cap, herein designated C, and three open top bottles, identical to those represented as A, but each having evaporation straws 90, 92, 94 similar in construction to that shown in FIGS. 1-3, but having various lengths depending on the bottle, herein designated D, E, and F, respectively.

With the exception of the evaporation control used, each of the plurality of bottles was identical having a total height of approximately 85 mm, of which approximately 13 mm comprises a top necked portion with the remaining 72 mm extending along a vertical cylindrical wall, the bottle having an overall interior diameter of 19.5 mm. The evaporation straw lengths used for this example were approximately 76 mm (3 inches) for bottle D, the evaporation straw 90 extending below the fluid surface to within about 2 mm of the bottom of the bottle, approximately 51 mm (2 inches) for bottle E, or in which the bottom of the straw 92 extended to approximately 8 mm above the top of the fluid level, and approximately 13 mm (0.5 inches) for bottle F, or in which the bottom of the straw 94 extended about 10 mm below the necked portion of the bottle. Each of the evaporation straws 90, 92, 94 were identical in construction with the exception of the length thereof and are defined by a plastic cylindrical hollow open-ended member that was inserted into the top opening of each corresponding bottle. That is, the straws 90, 92 and 94 have diameters sized to fit within the entirety of the open end of the bottles D, E and F, respectively.

Though not shown, the pierceable cap of bottle B, includes six slits in its top defining a plurality of flaps which open and close in a valve-like manner to permit the passage of a metering element, such as a metering tip. A number of small gaps exist between each of the flaps and the pierceable foil formed a 10 mm diameter hole which remained for the duration of the herein described test.

Two replicate bottles were run for each of the above noted conditions. The bottles were placed in a reagent supply in relation to a metering opening and 100 microliter amounts of sample were aspirated from each of the bottles using a 10 mm diameter disposable metering tip, such as the one previously shown in FIG. 1. In terms of exterior environment, the reagent supply (not shown) was placed in an environmental chamber at 70F/15%RH in order to maximize the amount of potential evaporation. Six replicate measurements were taken from each bottle initially (e.g., time zero) and after 3 days and 7 days, respectively.

According to this embodiment, the aspirated sample was dispensed into a reaction cuvette having a plurality of transparent wells, such as that described in copending U.S. application Ser. No. 09/897,673, where the absorbance of the sample was measured using a spectrophotometer (not shown). It should be readily apparent, however, that other testing apparatus can be utilized. None of the samples were mixed with any other fluid either prior to or during testing. The results of these tests is summarized in the following Table I.

to the bottle A from the preceding example. This bottle is an open top bottle having a height of 85 mm, an inside diameter of 19.5 mm and a top neck portion. The second bottle, herein designated H, has an inside diameter of 19.5 mm, but the total height of the bottle is only approximately 45 mm. The third and fourth bottles, herein designated I and J, respectively, were 85 mm in height but had a reduced (9.8 mm) inside diameter. Bottle J was further distinguished in that only 2 mL of fluid were used in order to increase the distance between the fluid surface and the opening at the top of the bottle as is clearly discerned from FIG. 9. Finally, the fifth bottle, herein designated as K, includes the same dimensions as bottle G, but also includes an evaporation straw 98, similar to those described above, which is inserted into the

TABLE I

| Bottle Type | Fluid Level Bottle | Bottle Type | Day 0 au's | Day 3 au's | Day 3% change | Day 3% evap/day | Day 7 au's | Day 7% change | Day 7% evap/day |
|---|---|---|---|---|---|---|---|---|---|
| A | 20 mL | open end - no evaporation control | 1.913 | 1.953 | 2.09 | 0.70 | 2.050 | 7.17 | 1.02 |
| A | 20 mL | open end - no evaporation control | 1.916 | 1.958 | 2.19 | 0.73 | 2.060 | 7.51 | 1.07 |
| B | 20 mL | pierceable cap | 1.915 | 1.945 | 1.57 | 0.52 | 2.014 | 5.15 | 0.74 |
| B | 20 mL | pierceable cap | 1.911 | 1.948 | 1.94 | 0.65 | 2.031 | 6.26 | 0.89 |
| C | 20 mL | foil cap | 1.902 | 1.929 | 1.42 | 0.47 | n/a | n/a | n/a |
| C | 20 mL | foil cap | 1.904 | 1.938 | 1.79 | 0.60 | 2.044 | 7.37 | 1.05 |
| D | 20 mL | 3" straw into fluid | 1.906 | 1.917 | 0.58 | 0.19 | 1.960 | 2.83 | 0.40 |
| D | 20 mL | 3" straw into fluid | 1.900 | 1.923 | 1.21 | 0.40 | 1.969 | 3.61 | 0.52 |
| F | 20 mL | 2" straw above fluid | 1.901 | 1.907 | 0.32 | 0.11 | 1.943 | 2.18 | 0.31 |
| E | 20 mL | 2" straw above fluid | 1.912 | 1.936 | 1.26 | 0.42 | 1.980 | 3.54 | 0.51 |
| F | 20 mL | 0.5" straw above fluid | 1.910 | 1.937 | 1.41 | 0.47 | 1.997 | 4.57 | 0.65 |
| F | 20 mL | 0.5" straw above fluid | 1.910 | 1.950 | 2.09 | 0.70 | 2.018 | 5.65 | 0.81 |

Figure 7:
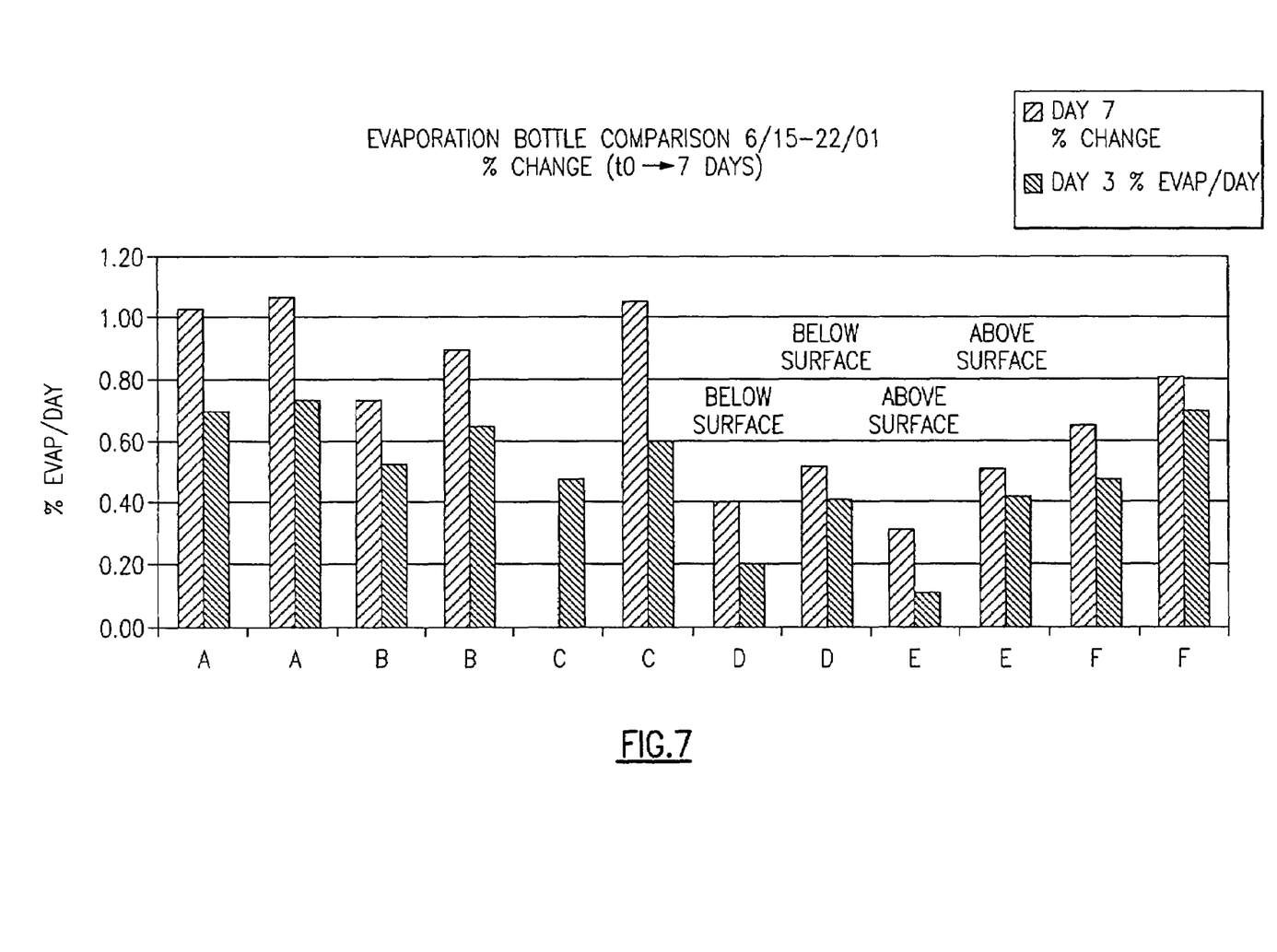
FIG. 7 is a pictorial view of the amount of evaporation rate change over time relative to the fluid supplies depicted in FIG. 6.

Referring to FIG. 7, the rate of evaporation for each bottle variation above is shown at day 3 and day 7 for each bottle tested.

It should be noted that the evaporation rates for the day 7 measurements is greater than that for day 3 due in part to the smaller amount of fluid which is remaining in the bottle in that each preceding test removes a quantity of fluid in order to make the absorbance measurements.

Figure 8:
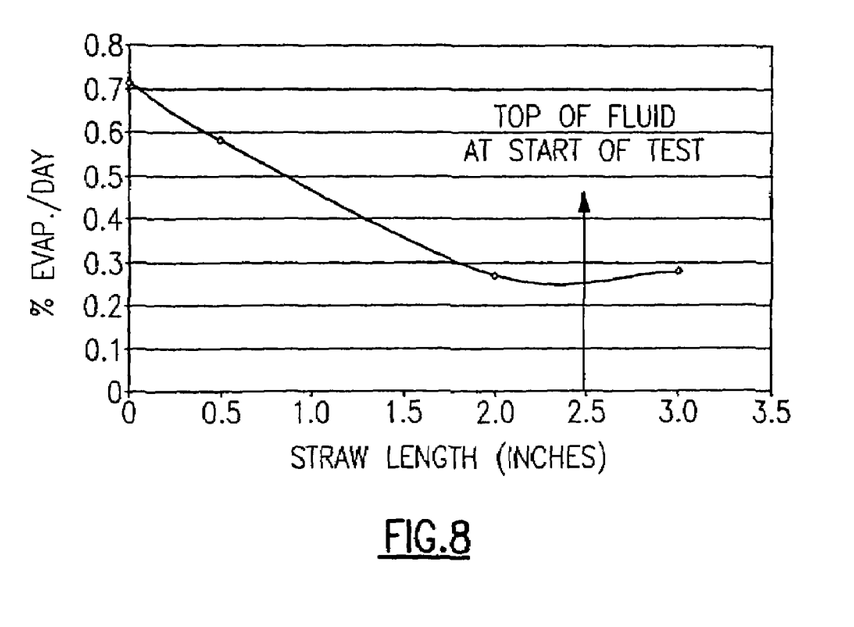
FIG. 8 is a graphical illustration of the effects of tube/diffusion length relative to evaporation control for the bottles depicted in FIG. 6.

In terms of an overall comparison, it can be seen that the pierceable and foil caps (bottles B and C) did have a reduced evaporation rate in comparison to bottle A, which had no evaporation control, of only about 20 percent. Bottles D, E, and F, however, each having an evaporation straw and an open top opening, each were more effective in reducing evaporation. As is clear from comparing bottles B, C, and F, however, the diffusion length (that is, the length of the tube) does not need to extend entirely or nearly entirely to the fluid surface in order to provide a degree of evaporation control which is superior to that of the pierceable and foil cap versions. It is equally clear, however, that having extending the diffusion length can further improve evaporation control dramatically, as is more clearly shown in FIG. 8.

EXAMPLE B

Comparison of Wetted Surface Area and Diffusion Length on Evaporation

Figure 9:
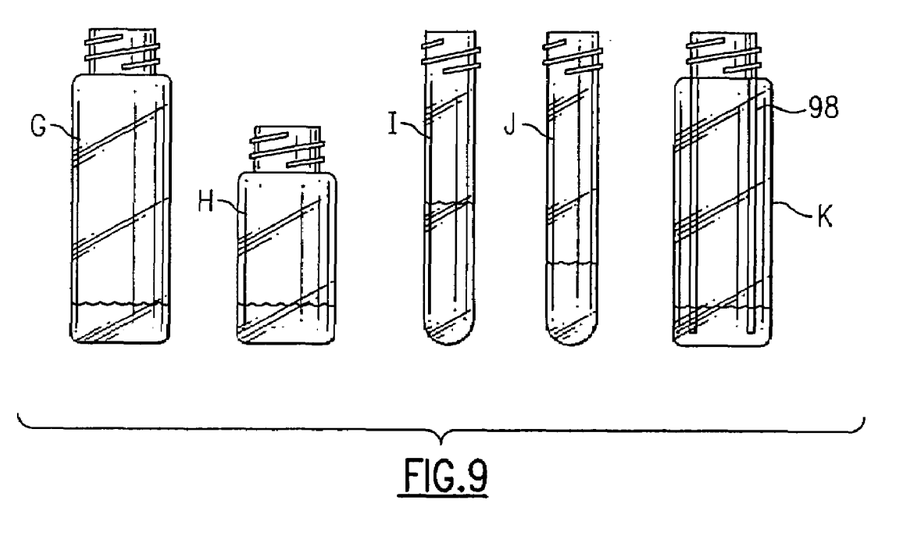
FIG. 9 is a front view of a second plurality of fluid bottles used for comparative testing.

As a further example, 4 mL of sample fluid was placed into another plurality of bottles as shown in FIG. 9. The sample fluid for purposes of this example was an identical solution, as defined in Example A, of 0.004% Magenta dye in water. For purposes of this example, different bottle-types, each having open ends, but different geometries, were compared. The first bottle, herein designated as G, is similar bottle interior. The straw 98 used in this example has a length which extends to within about 3 mm of the bottom of the bottle.

Six (6) replicate measurements were taken from each of the bottles initially (e.g., time zero) and after five days. For each test sample, 100 microliters of fluid was removed by conventional means from each bottle. As in the preceding, the absorbance of the fluid removed was measured using a spectrophotometer and the sample was not mixed with any other fluid during or prior to testing.

Two replicate bottles were run for each condition, wherein the bottles were contained within a reagent supply (not shown) and in relation to a metering opening within the cover thereof. As in the preceding example, the reagent supply was placed in an environmental chamber at 70F/15%RH to maximize the amount of potential evaporation.

The results of this testing is shown in the following Table II:

TABLE II

| | Wet Surface Area - $mm^2$ | Distance Fluid Surface to Bottle Opening - mm | % Evaporation/ Day |
|---|---|---|---|
| 4 mL in Std Bottle (19.5 mm Diameter) - Bottle G | 298 | 72 | 0.52 |
| 4 mL in Short version of Std Bottle (19.5 mm Diameter) - Bottle H | 298 | 27 | 2.30 |
| 4 mL in Narrow Bottle (9.8 mm Diameter) Bottle I | 75 | 30 | 0.73 |
| 2 mL in Narrow Bottle (9.8 mm Diameter) Bottle J | 75 | 57 | 0.27 |

TABLE II-continued

| | Wet Surface Area - mm² | Distance Fluid Surface to Bottle Opening - mm | % Evaporation/ Day |
|---|---|---|---|
| 4 mL in Std Bottle w/Straw Tube (9.8 mm Diameter Inserted) - Bottle K | 75 | 72 | 0.04 |

Bottles G, H, and K include the same wetted surface area except that the inserted evaporation straw 98 of bottle K, extending well into the fluid surface, essentially caps the contained fluid which is on the outside of the tube and produces a drastic reduction of about 75 percent of exposed wetted surface area. A reduction in the amount of exposed fluid surface area produces an expected change (decrease) in evaporation rate. However, this testing further confirms that nearly similar or improved reductions can occur by increasing the distance of the fluid surface from the mouth of the bottle opening (e.g., the diffusion length). For example and using the above bottle designs, an increase of 42 mm of vertical distance can compensate for having an exposed fluid surface that is 4 times larger in area. The relative relationships of wet surface area and distance of the fluid distance on evaporation rates are further shown graphically in FIG. 10 which illustrates that diffusion length can have a more profound effect on larger diameter areas. It is submitted, however, that this relationship is limited to creating or defining a stagnant zone; that is, one which is not subjected to convective or other similar effects that will effectively negate the relationships herein described.

Figure 11:
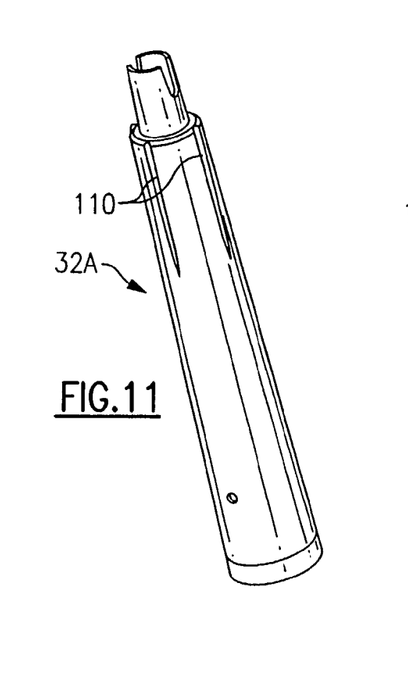
FIG. 11 is a side perspective view of a fluid evaporation control element according to a another preferred embodiment of the invention.

Though a design having a minimum diameter for a maximum of length is preferred for the evaporation control element, based on the above relationships, there are reasons for providing a tapering design. One reason as previously noted, in the mouth of the bottle, presents added clearance to permit a metering element to be located within the control element from the metering mechanism. Referring to FIG. 11, the tapered design of the evaporative control element 32A of FIG. 1 further permits stacking of the elements prior to insertion. Inclusion of at least one outer rib 110 assists in the stacking of the elements to prevent jamming and also provides a maximum insertion depth when stacking.

Utilizing the above data, it can be shown that effective evaporation control can be achieved without requiring a bottle having an inserted evaporation control element as previously described above.

Figure 12:
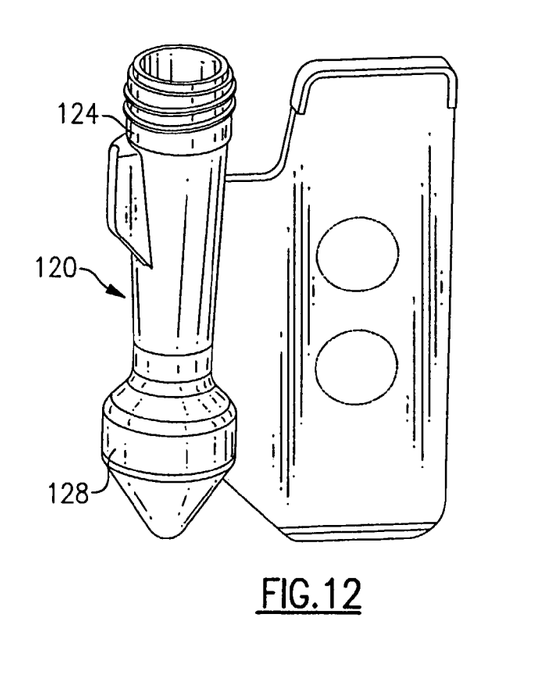
FIG. 12 is a side perspective view of a fluid supply made in accordance with another preferred embodiment of the invention.
Figure 13:
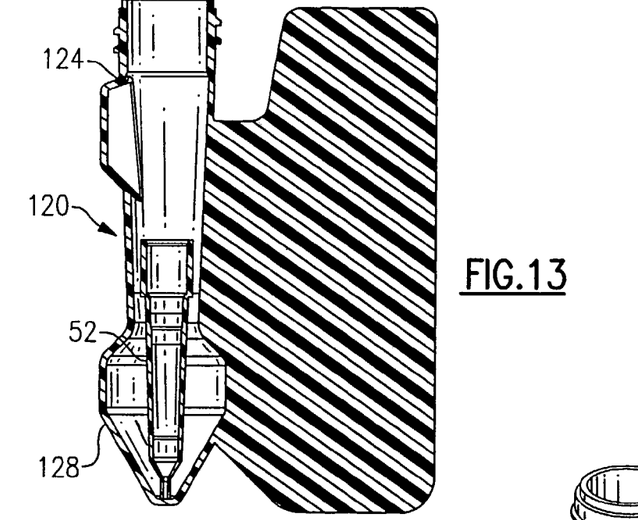
FIG. 13 is a side view taken in section of the fluid supply of FIG. 12.

Referring to FIGS. 12 and 13, a bottle 120 is herein described having a design which mimics aspects of the above described evaporation straw concept. According to this embodiment, the upper end 124 of the bottle 120 contains an open mouth having an inner diameter, the diameter of the interior of the bottle having an inward taper extending from an upper portion extending to a narrowed minimum inner diameter in an intermediate portion thereby defining a-diffusion length to the level of fluid contained therein immediately preceding a substantially wider lower fluid retaining section 128. Though this design does not address a reduction of wetted exposed fluid surface area as accomplished directly by the straw concept described above, the reduced diameter in the intermediate portion of the bottle, which is reduced sufficiently to permit a metering tip 52 to pass therethrough and the increased diffusion length, provides substantial evaporative controls.

Figure 10:
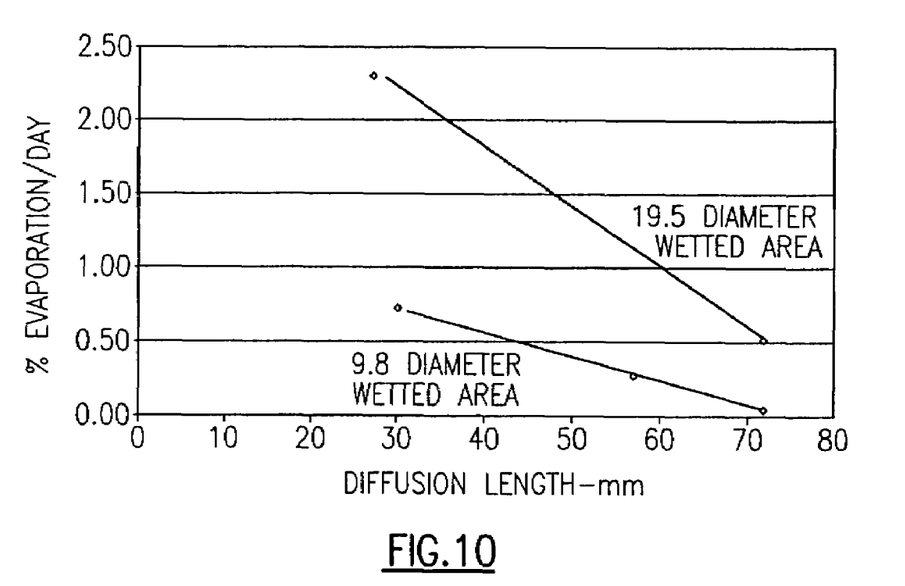
FIG. 10 is a graphical illustration of the effects of tube/diffusion length and exposed fluid surface area relative to the fluid supplies of FIG. 9.

That is, the narrowed diameter of the intermediate portion of the bottle immediately over the lower fluid retaining portion 128 creates an extended "stagnant" diffusion area that provides adequate evaporation control. Dimensionally, the herein described bottle 120 has an overall height of about 83 mm, wherein the diameter of the bottle at the mouth is approximately 13 mm and narrows to about 10 mm at its narrowest point to permit the passage therethrough of a metering element 52 of about 10.5 mm. It should be noted that the bottle could preferably made with the substantially narrow diameter over the entire length of the upper and intermediate portions, in this instance about 54 mm, wherein the inner diameter of the fluid retaining portion immediately beneath the narrowed inner diameter in the intermediate portion expands to about 25 mm. It has been observed as from the preceding data that providing a bottle design with a minimum diameter immediately prior to the fluid retaining portion of the bottle produces significantly better evaporation control than attempting to control the exposed wetted area and as shown in FIG. 10, increasing the distance between the mouth of the bottle (e.g. the environment) and particularly providing a narrowed diameter above or preferably immediately above the exposed fluid to creating a stagnant zone above the fluid produces larger evaporation controls even if wetted fluid areas are increased.

While the present invention has been particularly shown and described with reference to the preferred mode as illustrated in the drawing, it will be understood by one skilled in the art that various changes in detail may be effected therein without departing from the spirit and scope of the invention as defined by the claims.

PARTS LIST FOR FIGS. 1-13

| | |
|---|---|
| 10 | reagent pack |
| 14 | support |
| 20 | bottle |
| 24 | top opening |
| 28 | hollow interior |
| 32 | evaporation control element |
| 32A | evaporation control element |
| 33 | upper end |
| 35 | bottom end |
| 36 | cylindrical wall |
| 40 | tapered bottom |
| 44 | top necked portion |
| 48 | exterior cap threads |
| 52 | disposable metering tip |
| 64 | narrowed bottom portion |
| 66 | stepped portion |
| 68 | aligned cutouts |
| 72 | vent hole |
| 76 | annular tab |
| 80 | circumferential slot |
| 90 | evaporation straw |
| 92 | evaporation straw |
| 94 | evaporation straw |
| 98 | evaporation straw |
| 110 | outer rib |
| 120 | bottle |
| 124 | upper end |
| 128 | fluid retaining section |
| A | bottle |
| B | bottle |
| C | bottle |
| D | bottle |
| E | bottle |
| F | bottle |
| G | bottle |
| H | bottle |
| I | bottle |
| J | bottle |

-continued

PARTS LIST FOR FIGS. 1-13

| K | bottle |
|---|---|
| 140 | proboscis |
| 150 | metering mechanism |
| 160 | reagent supply |
| 164 | rotatable wheel |

Though only certain particular embodiments have been described herein, it should be readily apparent that variations and modifications are possible in accordance with the ambits of the concepts presented. For example, and though the present invention related mainly to a discussion of reagent containing vessels, it should be contemplated that other fluid containing vessels, such as those containing calibration liquids or other sample fluids can utilize the concepts described herein.

We claim:

1. A clinical analyzer comprising:
a metering apparatus having a proboscis and at least one fluid aspirating element attached thereto; and
a reagent fluid supply apparatus, said reagent fluid supply apparatus comprising:
a flat planar support;
a bottle integral with said flat planar support along one side thereof, said flat planar support including a vertically extending wall extending along substantially the height of said bottle, said support further including a horizontal base surface that is substantially coplanar with the bottom of said bottle, said bottle defined by an interior that retains a predetermined quantity of reagent fluid within a lower fluid retaining portion of said bottle and receives a fluid aspirating element attached to said proboscis of said metering apparatus of said clinical analyzer in order to periodically remove a portion of said quantity of reagent fluid, said bottle including an open top, an upper portion and an intermediate portion disposed above said lower fluid retaining portion, each of said upper and intermediate portions including an inwardly narrowing inner diameter that tapers from a maximum diameter at said open end of the bottle to a minimum inner diameter at the bottom of the intermediate portion adjacent the top of the lower fluid retaining portion, said lower fluid retaining portion having an inner diameter at the top of the fluid retaining portion that is larger than the inner diameter of the open end of said bottle such that a stagnant diffusion zone is created by said upper and intermediate portions, said stagnant diffusion zone extending over a diffusion length between approximately the top of the fluid level within the lower fluid retaining portion and the open top of the bottle, thereby preventing evaporative effects of reagent within said bottle during and between metering events.

2. A clinical analyzer as recited in claim 1 wherein the minimum inner diameter of said bottle within said intermediate portion is sized to permit the passage of said fluid aspirating element as attached to said metering apparatus to permit a distal end of said fluid aspirating element to be positioned in proximity with a bottom surface of said bottle to permit aspiration of fluid from the lower fluid-retaining portion of said bottle.

3. A clinical analyzer as recited in claim 2, wherein said fluid aspirating element is a disposable metering tip.

4. A clinical analyzer as recited in claim 1, wherein the stagnant diffusion zone extends over a diffusion length that extends at least one half of the overall height of said bottle.

5. A reagent supply apparatus that is used within a clinical analyzer, said apparatus comprising:
a rotatable wheel;
at least one reagent pack disposed within said rotatable wheel, said at least one reagent pack including:
a flat planar support; and
a bottle integral with said flat planar support along one side thereof, said flat planar support including a vertically extending wall extending along substantially the height of said bottle, said support further including a horizontal base surface that is substantially coplanar with the bottom of said bottle, said bottle defined by an interior that retains a predetermined quantity of reagent fluid within a lower fluid retaining portion of said bottle and receives a fluid aspirating element from a metering apparatus of said clinical analyzer in order to periodically remove a portion of said quantity of reagent fluid, said bottle including an open top, an upper portion and an intermediate portion disposed above said lower fluid retaining portion, each of said upper and intermediate portions including an inwardly narrowing inner diameter that tapers from a maximum diameter at said open end of the bottle to a minimum inner diameter at the bottom of the intermediate portion adjacent the top of the lower fluid retaining portion, said lower fluid retaining portion having an inner diameter at the top of the fluid retaining portion that is larger than the inner diameter of the open end of said bottle such that a stagnant diffusion zone is created by said upper and intermediate portions, said stagnant diffusion zone extending over a diffusion length between approximately the top of the fluid level within the lower fluid retaining portion and the open top of the bottle.

* * * * *